(12) United States Patent
Sadegh et al.

(10) Patent No.: US 8,082,802 B1
(45) Date of Patent: Dec. 27, 2011

(54) COMPACT AND STAND-ALONE COMBINED MULTI-AXIAL AND SHEAR TEST APPARATUS

(75) Inventors: Ali M. Sadegh, Franklin Lakes, NJ (US); Paul V. Cavallaro, Raynham, MA (US); Claudia J. Quigley, Lexington, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 347 days.

(21) Appl. No.: 12/587,329

(22) Filed: Sep. 25, 2009

Related U.S. Application Data

(60) Provisional application No. 61/215,967, filed on Apr. 28, 2009.

(51) Int. Cl.
*G01N 3/02* (2006.01)
(52) U.S. Cl. .......................... 73/856; 73/760
(58) Field of Classification Search ............... 73/760, 73/855–859
See application file for complete search history.

(56) References Cited

U.S. PATENT DOCUMENTS

| | | | |
|---|---|---|---|
| 3,803,373 A * | 4/1974 | Schilke et al. ............... 200/52 R |
| 3,841,619 A * | 10/1974 | Hickman ..................... 269/244 |
| 4,010,502 A * | 3/1977 | Cushing et al. ................ 12/86.7 |
| 4,406,584 A * | 9/1983 | Stepp ............................ 416/41 |
| 4,588,091 A * | 5/1986 | Wade ............................ 209/546 |
| 5,044,144 A * | 9/1991 | Foote et al. .................... 53/456 |
| 5,881,661 A * | 3/1999 | Lawendowski et al. . 112/470.03 |
| 6,113,350 A * | 9/2000 | Liu ................................ 416/11 |
| 6,182,839 B1 * | 2/2001 | Robbins et al. ................ 211/78 |
| 6,860,156 B1 * | 3/2005 | Cavallaro et al. .............. 73/819 |
| 6,864,984 B2 * | 3/2005 | Naya et al. .................... 356/445 |
| 7,051,600 B1 * | 5/2006 | Cavallaro et al. ........ 73/862.041 |
| 7,204,160 B1 * | 4/2007 | Sadegh et al. ........... 73/862.041 |

* cited by examiner

*Primary Examiner* — Max Noori
(74) *Attorney, Agent, or Firm* — James M. Kasischke; Michael P. Stanley; Jean-Paul A. Nasser

(57) ABSTRACT

A testing apparatus is disclosed that includes a turntable, an upper scissor jack assembly and a lower scissor jack assembly positioned in parallel planes, about a longitudinal axis and affixed to a base. The apparatus is powered by at least three motors with supporting controllers. The lower assembly is affixed to the base mechanically via the turntable which allows the lower assembly to rotate with respect to the upper assembly. There are two loading plates attached to the hinges of each scissor jack. The test specimen is secured by the loading plate. Each scissor jack operates by a screw-gear powered by one of the motors. Upon energizing a stepper motor; the screw-gear positions a scissor jack to apply a tension or compression on the specimen. While subjected to tension or compression, the lower jack assembly can be rotated with respect to the upper assembly for in-plane shear loading.

22 Claims, 12 Drawing Sheets

COMPACT AND STAND-ALONE COMBINED MULTI-AXIAL AND SHEAR TEST APPARATUS

This application claims the benefit of U.S. Provisional Patent Application Ser. No. 61/215,967 filed on Apr. 28, 2009 and entitled "Compact and Stand-Alone Combined Multi-Axial and Shear Test Apparatus" by the inventors, Paul V. Cavallaro, Ali Sadegh and Claudia Quigley.

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention relates generally to a compact, stand-alone in-plane shear loading and biaxial tension or compression testing apparatus employable for studies of the mechanical properties of materials such as metals, plastics and composites.

(2) Description of the Prior Art

Fabrics typically used in air-inflated structures (air beams, temporary shelters, tents, temporary bridges, and space structures) are often manufactured in woven or braided forms. These structures rely on inflation pressure to pre-tension the fabric (or membrane) so that the necessary planar stiffness can be developed to achieve rigidity and resistance to in-plane and lateral loads.

Unlike metallic structures, air-inflated structures are designed to be lightweight; to have deployed-to-stowed volume ratios that can be in the range of 1000-to-1; and possibly be self-erecting. Although these technologies have been known in the art for many years, the technologies have not been refined to a level that reliable structures can be designed by structural analysis.

The advent of fiber-based structural material and weaving/braiding technologies has improved the load carrying capacity of pressurized structures. Accordingly, there has been increasing interest in modeling the mechanical behavior of woven fabrics. However, this class of composite material has complex microstructures that can produce complex mechanical responses. In particular, the mechanical characteristics of plain-woven fabrics used in inflated structures (unlike traditional composite materials) exhibit high non-linearity with a dependence on the internal pressure and contact interactions within the woven fabric.

Therefore, there is a need for a testing apparatus which allows the measurement of the elastic and shear moduli for air beams. Specifically, the need is for a compact and independent testing apparatus that is capable of applying a combined in-plane shear load and biaxial load. This need includes the capability of loading non-orthogonal composite or fabric materials with equi biaxial or non-equi biaxial loading.

While biaxial testing apparatuses with compression and tension loading or in-plane shear testing apparatuses exist in the prior art, only those disclosed in U.S. Pat. Nos. 6,860,156, 7,051,600 and 7,204,160 to Cavallaro et. al have a combined feature of in-plane shear and compression/tension testing capabilities and the capability to apply a non-orthogonal biaxial loading.

Cavallaro et al., (U.S. Pat. No. 6,860,156), describes a multi-axial tension or compression and an in-plane shear loading testing apparatus in which the apparatus is capable of determining the mechanical properties of metal, plastic, woods, fabrics, elastomers and other materials. The testing apparatus uses a mechanical testing machine for applying the tension, compression and rotation loading on the apparatus. The loading is applied to the test specimen in a displacement-controlled mode by which an equal biaxial extension (or contraction) results.

Sadegh et al, (U.S. Pat. No. 7,204,160), describes a combined multi-axial tension or compression and in-plane shear loading apparatus with a choice of displacement-controlled or force-controlled modes of loading. This apparatus improves upon the apparatus of (U.S. Pat. No. 6,860,156) and can be used to subject a test specimen to proportionately controlled loads among the axial directions. The force control feature is crucial in creep testing of composite, anisotropic and fabric materials, wherein constant tension or compression forces on the test specimen is desired.

Cavallaro et al. (U.S. Pat. No. 7,051,600) describes a testing apparatus capable of simultaneously applying a three-dimensional tension or compression state of stress combined with in-plane shear loading in a displacement-controlled mode. This apparatus improves over the previous apparatus in which of U.S. Pat. No. 6,860,156 in which the compression and tension was in only in two dimensions (planar). That is, the test specimen could be subjected to tension, compression, independently or simultaneously, in the three orthogonal directions, X, Y and Z, with the specimen optionally subjected to a shear load in one plane. A restriction of the apparatus is the required use of a mechanical testing machine for applying the tension, compression and rotation loading to the apparatus.

Instead prior art methods have employed two or more separate actuators in complex test fixtures and/or pressurization techniques for applying a biaxial load to a test specimen. A disadvantage of these methods is the need for two or more loading devices and the relatively high cost of the equipment.

U.S. Pat. No. 5,905,205 describes an in-plane biaxial test apparatus comprising a rhombus and linkages to transfer the load to the orthogonal direction of the loading. The disadvantage of this apparatus is that the apparatus is not capable of applying in-plane shear to the test specimen. Another disadvantage of this apparatus is that the biaxial loading is limited to an orthogonal configuration.

Lynch et al. (U.S. Pat. No. 3,776,028) describes an apparatus requiring three independent loading mechanisms. The test fixture of Lynch is a load point application device that is used to position the application of a single point force acting normal to a flat rectangular panel (specimen) such as those found in aircraft structures. The device does not enable the application of multi-axial tension/compression forces in optional combination with in-plane shear forces.

U.S. Pat. No. 4,192,194, describes an apparatus for bi-axially loading a specimen through pressurizing the inside surface of a cylinder. The disadvantage of this apparatus includes the requirement of cylindrical shape of the specimen and the high cost and added equipment of pressurization.

Simonelli et al (U.S. Pat. No. 5,913,246) does not enable multi-axial loads (tension-tension, tension-compression, compression-compression) applied simultaneously along orthogonal or oblique orientations with or without in-plane shear regardless of the shape of the test specimen.

Other prior art reference include U.S. Pat. No. 5,448,918 which describes an apparatus with X-shape that is only used for compression load and U.S. Pat. No. 5,279,166 which describes an apparatus for self-alignment of a biaxial loading device. U.S. Pat. No. 5,144,844 describes a cruciform planar specimen for biaxial material testing.

Although the advantages over the prior art by the cited Cavallaro and Sadegh references are numerous, a significant disadvantage is that the apparatuses of the cited references require a mechanical testing machine with the capabilities of applying tension, compression and rotation loading. That is, to use any apparatus of the cited patent references, one needs to acquire the mechanical testing machine. The machine can be costly and requires a large space for operation.

Thus, there is a need for a compact, comparatively low cost and stand-alone material testing apparatus that is capable of applying combined multi-axial tension/compression and in-plane shear loads to a specimen in displacement-controlled or force-controlled modes without requiring a materials testing machine for the operation of the apparatus.

SUMMARY OF THE INVENTION

It is therefore a general purpose and primary object of the present invention to provide a compact, low cost and stand-alone material testing apparatus that is capable of applying combined multi-axial tension/compression and in-plane shear loads to a test specimen in optional displacement-controlled or force-controlled modes without requiring a materials testing machine for operation of the apparatus.

It is a further object of the present invention to provide, independently and without the need for a testing machine, the ability to test a specimen by subjecting the specimen to a combined in-plane, compression or tension as well as in-plane shear.

In order to attain the objects described, the present invention relates generally to a combined (simultaneously or independently) in-plane shear and compression or tension loading of a test specimen such as but not limited to metals, plastics, composites, woods, fabrics or anisotropic materials. The apparatus is self-contained to operate independent of an external testing device. The apparatus can apply unequal, orthogonal or oblique stress states on a specimen by the use of load transfer systems comprising two rhombus-shaped scissor jack assemblies and a turntable.

The apparatus provides flexibility in applying an unequal biaxial load to the specimen by applying different torque to each scissor jack assembly. In addition, the apparatus provides further flexibility in applying an orthogonal biaxial loading by choosing a different angle, other than orthogonal between the scissor jack assemblies. The in-plane shear load can be applied either simultaneously or independently of the biaxial tension/compression load.

The apparatus comprises a lower scissor jack assembly, an upper scissor jack assembly, at least four loading plates, stepper electric motors and controls, a turntable and a fixed support base. Each scissor jack assembly includes a rhombus-shape linkage system, at least one power screw-gear, loading plate assemblies and loading supports.

The upper scissor jack assembly is supported above the fixed base and the lower scissor jack assembly is positioned on the turntable. The turntable engages with a stepper motor to rotate in alternating directions with respect to the base. By rotating the turntable, the lower scissor jack assembly rotates relative to the upper scissor jack assembly. The angle of rotation of the lower scissor jack assembly can be measured directly.

The linkage system of the upper scissor jack assembly has four hinges, two hinges at either side of the screw-gear and the other two hinges that are connected to two linkages of the upper scissor jack assembly. One of the stepper motors is axially connected to the power screw-gear. Two hinges at either side of the screw-gear are restrained to move in an expansion and/or a contraction mode in collinear slots located on the support brackets. The other two hinges are restrained by co-linear sliding shafts that are supported by fixed brackets. The co-linear slots (for the screw-gear hinges) are perpendicular to the axis of the co-linear sliding shafts. Upon energizing the stepper motor, the screw-gear hinges along the screw-gears move within the slots, and the adjacent loading hinges move perpendicularly along the sliding shaft while the center of the upper scissor jack assembly remains fixed.

Likewise, the linkage system of the lower scissor jack assembly has four hinges, two at either side of the screw-gear and the other two hinges connecting the two linkages. The second stepper motor is axially connected to the power screw-gear of the lower scissor jack assembly. All hinges of the lower scissor jack assembly are restrained to move in four slots (two co-linear pairs) on the turntable. The co-linear slots are perpendicular allowing the adjacent hinges, screw-gear hinges and loading hinges, to move in perpendicular directions in an expansion and/or contraction mode. Upon energizing the stepper motor of the lower scissor jack assembly, all hinges move along their corresponding slots in a perpendicular manner while the center of the lower scissor jack assembly remains fixed at a center point that is vertically below the center point of the upper scissor jack assembly.

Each of the loading plates comprises a L-shaped bracket and a gripping/clamping means that is attached to the distal end of the bracket. The loading plates are attached to the two loading hinges of the upper scissor jack assembly and extend below the plane of the upper scissor jack assembly. Likewise, another set of loading plates are connected to the loading hinges of the lower scissor jack assembly and extend above the plane of the lower scissor jack assembly.

The plane of the clamp mechanism of the sets of the loading plates is co-planar. That is, when the four sides of the test specimen are clamped by the loading plates; the test specimen remains horizontal. Because the center point of the two scissor jacks are fixed in space and are located parallel to each other; the center point of the specimen remains fixed while the specimen is subjected to tension or compression.

The output shaft of a third stepper motor is connected to a gear that engages with a larger gear with the axle of the larger gear connected to the turntable. Upon energizing the stepper motor, the turntable rotates with respect to the base. The stepper motors are electrically connected to corresponding motor drivers. Each driver is electrically connected to a data acquisition device which is connected to a computer. Through simple programming, one can control the use of the stepper motors; thereby, applying a tension, compression and rotation to the specimen at varying testing levels.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

Figure 1:
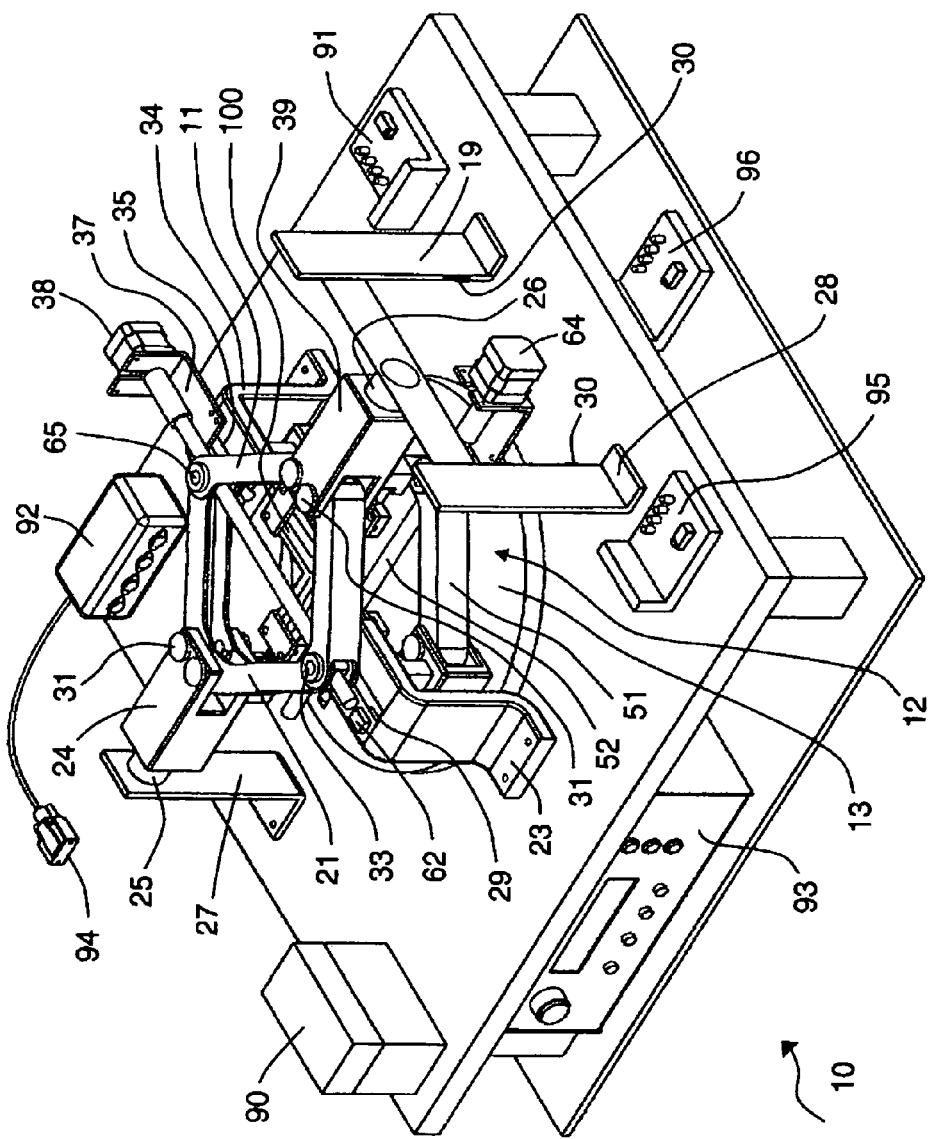
FIG. 1 depicts a perspective view of one embodiment of the testing apparatus of the present invention with a test specimen positioned within the apparatus.
Figure 2:
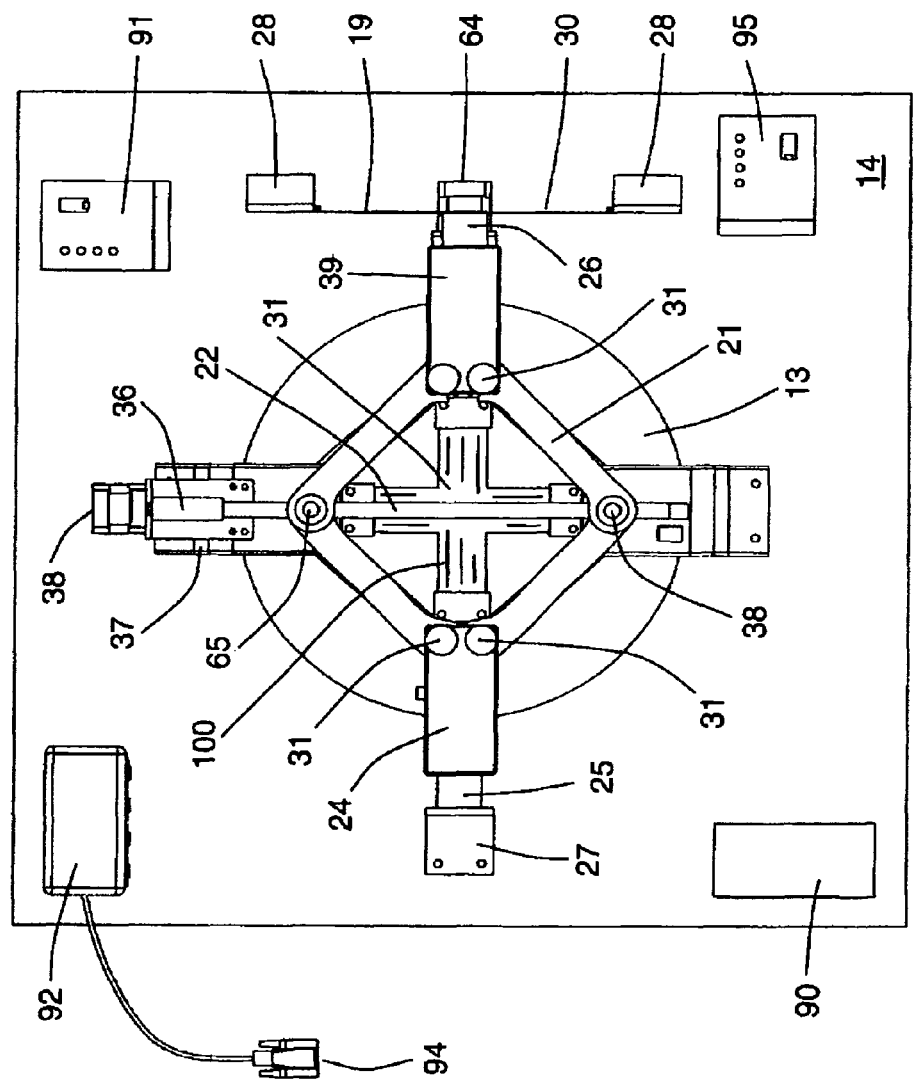
FIG. 2 depicts a top view of the testing apparatus of FIG. 1.
Figure 3:
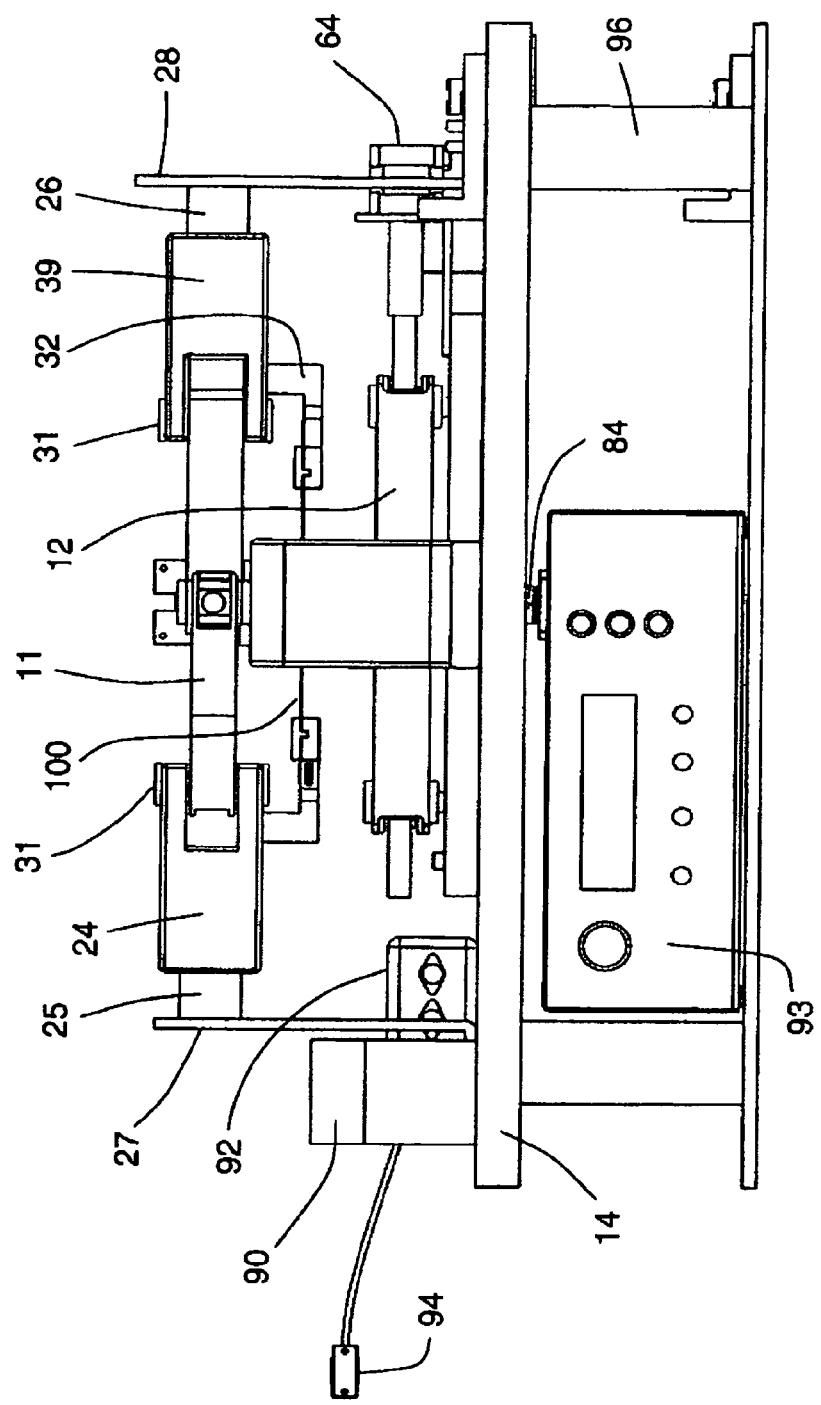
FIG. 3 depicts a side view of the testing apparatus of FIG. 1.

Referring now to FIGS. 1-3, a compact testing apparatus 10 is shown in which the apparatus comprises an upper scissor jack assembly 11, a lower scissor jack assembly 12, a turntable 13 and a support base 14 (preferably sized for tabletop use). For testing, a test specimen 100 is positioned within the apparatus 10.

The upper scissor jack assembly 11 comprises a four-bar linkage 21, hinged in a rhombus shape (similar to an automotive scissor jack) and a power (lead) screw-gear 22. The four hinges of the upper jack assembly 11 are supported by upper assembly support brackets 23, 27, 28 and 34 in which the support brackets are rigidly connected to the fixed base 14.

The screw-gear 22 is activated by a first stepper motor 38 that is controllable by a computer (not shown) thru an electronic driver 91, a data acquisition board 92 and a serial port 94.

The lower scissor jack assembly 12, similar to the upper scissor jack assembly 11, comprises a four bar linkage 51 hinged in a rhombus shape and a power (lead) screw-gear 52. The hinges of the lower scissor jack assembly 12 are supported by the turntable 13. The screw-gear 52 of the lower scissor jack assembly 12 is activated by a second stepper motor 64 that is computer-controlled through the serial port 94, the data acquisition board 92 and an electronic driver 95. The turntable 13 is activated by a third stepper motor 84 that is computer-controlled through the serial port 94, the data acquisition board 92 and an electronic driver 96.

The testing apparatus 10 also includes a strain indicator 90 that is electrically connected to at least four strain gauges 75 (See FIG. 8) in which the gauges measure the strain subjected by the test specimen 100. In addition, the testing apparatus 10 has a standard power supply 93 for the data acquisition board 92, the electronic drivers 91, 95 and 96 and the strain indicator 90.

Figure 4:
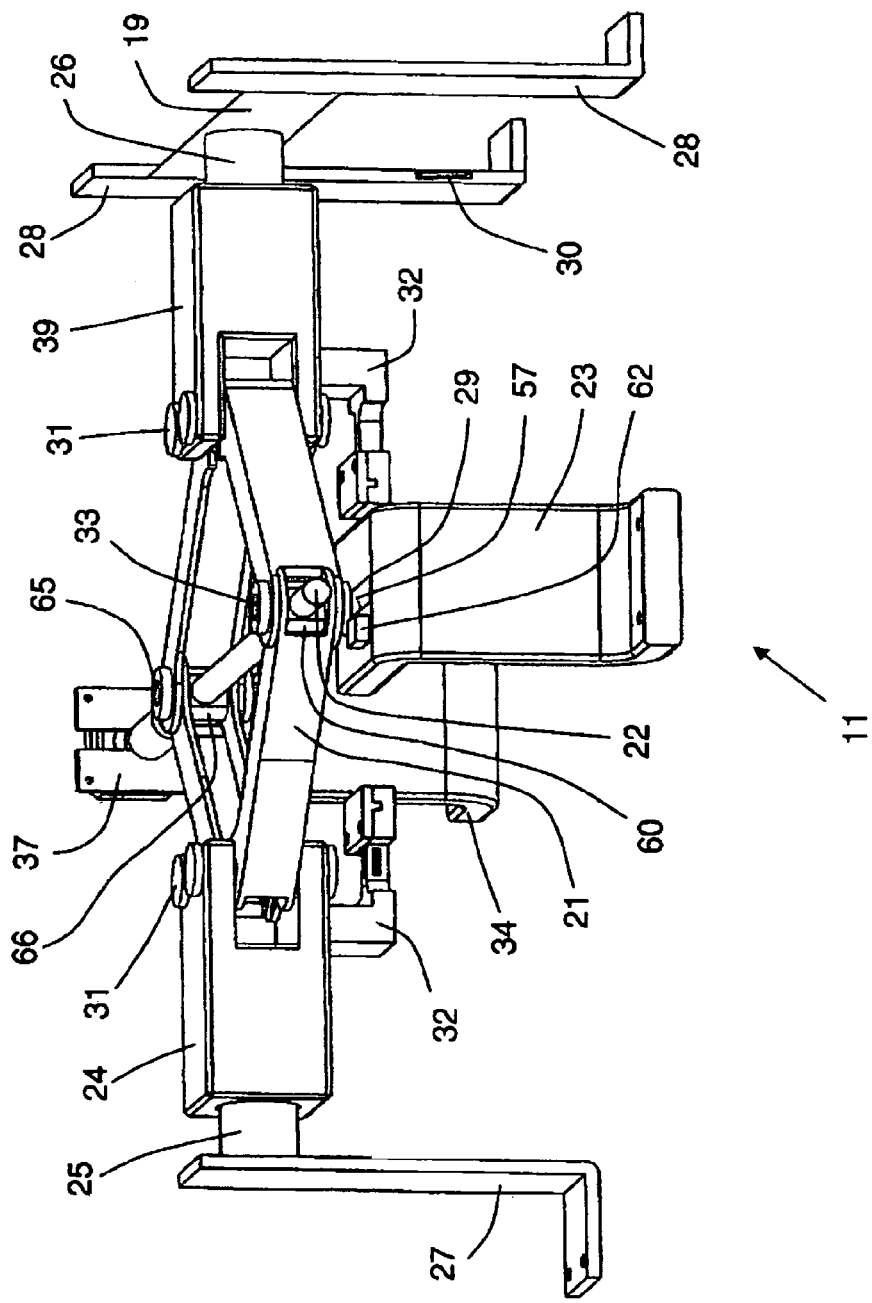
FIG. 4 depicts a perspective view of the upper scissor jack assembly and loading plates of the testing apparatus of FIG. 1.

Referring now to FIG. 4, the four linkages 21 of the upper scissor jack assembly 11 are hinged at screw-gear hinges 33 and 65 and at loading hinges 31. The loading hinges 31 are connected to loading supports 24 and 39 on either side of the loading hinges.

The loading support 24 is axially engaged with a sliding shaft 25 that is rigidly connected to the support bracket 27 such that the loading support can slide axially over the shaft. The loading support 39 is axially engaged with a sliding shaft 26 that is rigidly connected to a horizontal connector 19 and the vertical support brackets 28. The loading support 39 can slide axially over the sliding shaft 26. Both the sliding shafts 25 and 26 restrain the displacement of the loading hinges 31 to a co-linear motion that is perpendicular to the axis of the screw-gear 22.

The screw-gear hinge 33 that is located at the proximal end of the screw-gear 22 has a nut 60 that is engaged with the screw-gear and a displacement pin 57 that slides linearly in a slot (indent) 29 that is located on the horizontal plane of the support 23.

The screw-gear hinge 65 that is located at the distal end of the screw-gear 22 has a nut 66 that is engaged with the screw-gear and the pin 57 that slides linearly in a slot (indent) 35 (See FIG. 1) in which the slot is located on the horizontal plane of the upper assembly support bracket 34. The slots 29 and 35 restrain the displacement of the screw-gear hinges 33 and 65 to a co-linear motion that is perpendicular to a reference line indicating a position of the loading hinges 31. The support brackets 23 and 34 are rigidly connected to the base 14.

The upper scissor jack assembly 11 also has two loading plate assemblies 32 that are rigidly attached to the loading supports 24 and 39. The loading plate assemblies 32 extend below the plane of the upper scissor jack assembly 11 such that when two ends of the test specimen 100 are clamped to the distal ends of the loading plates; the specimen does not contact the screw-gear 22.

Figure 11:
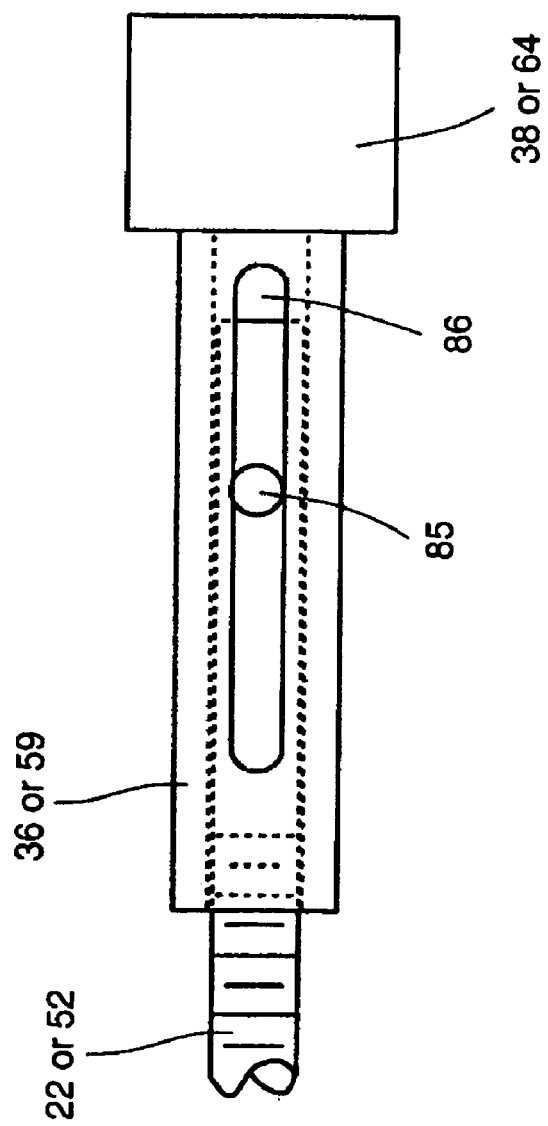
FIG. 11 depicts a sliding coupling connection joining a stepper motor to a power screw-gear.

In the figure, the first stepper motor 38 is shown mounted on a motor support bracket 37 and to the upper assembly support bracket 34; however the first stepper motor may be directly affixed to the base 14. The shaft of the stepper motor 38 is axially and operationally connected to the power screw-gear 22 through a coupling shaft 36. The coupling shaft 36 has a pin 85 and a slot 86 (See FIG. 11) that transfers the torque of the shaft of the stepper motor 38 to the power screw-gear 22 while allowing limited axial displacement between the shaft and the screw-gear. There is a limiting switch 62 on the proximal end of the slot 29 that stops the stepper motor 38 when the hinge reaches the proximal end of the slot; thereby, preventing the upper scissor jack assembly 11 from overextending.

Figure 5:
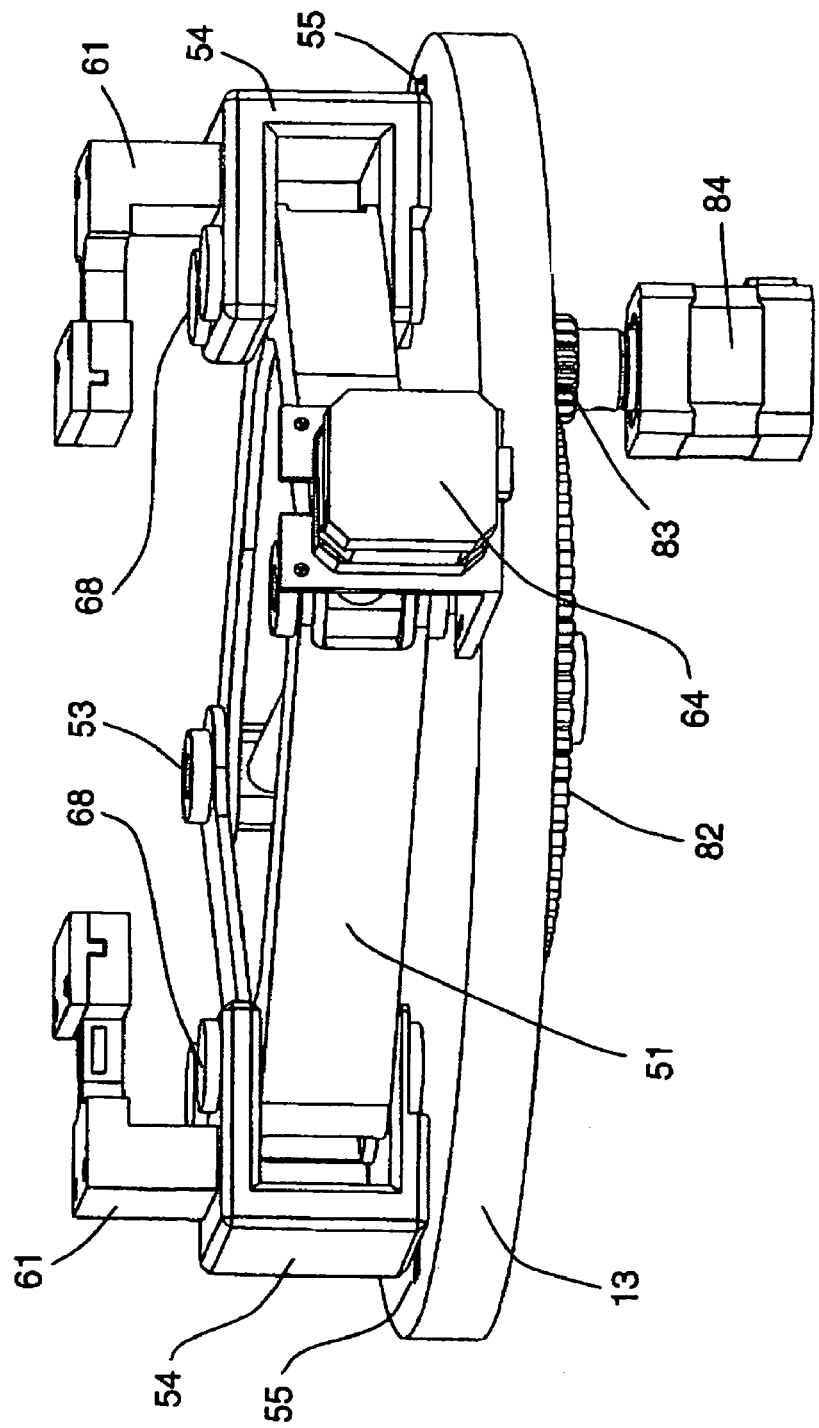
FIG. 5 depicts a perspective view of the lower scissor jack assembly and loading plates on a turntable with the gear system of the testing apparatus of FIG. 1.
Figure 6:
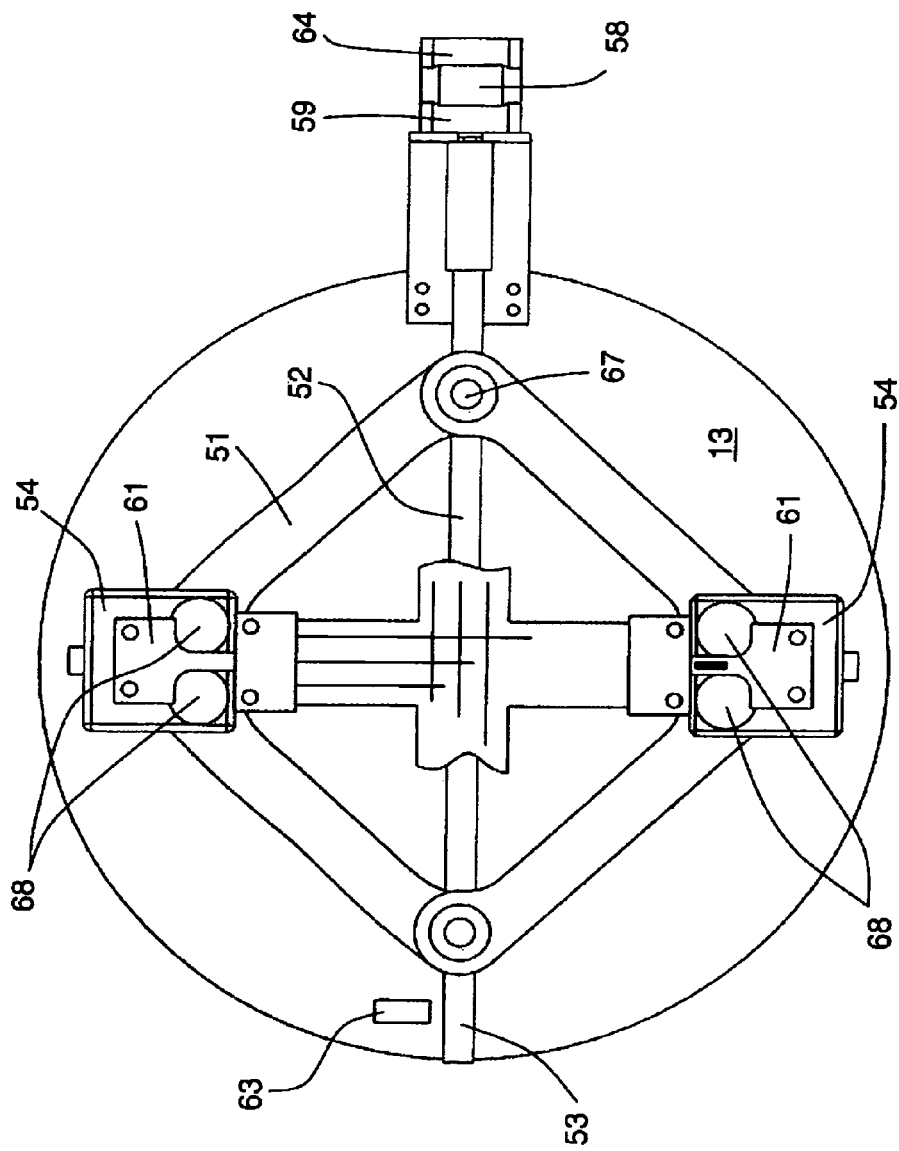
FIG. 6 depicts a top view of the lower scissor jack assembly and the turntable of the testing apparatus of FIG. 1.
Figure 7:
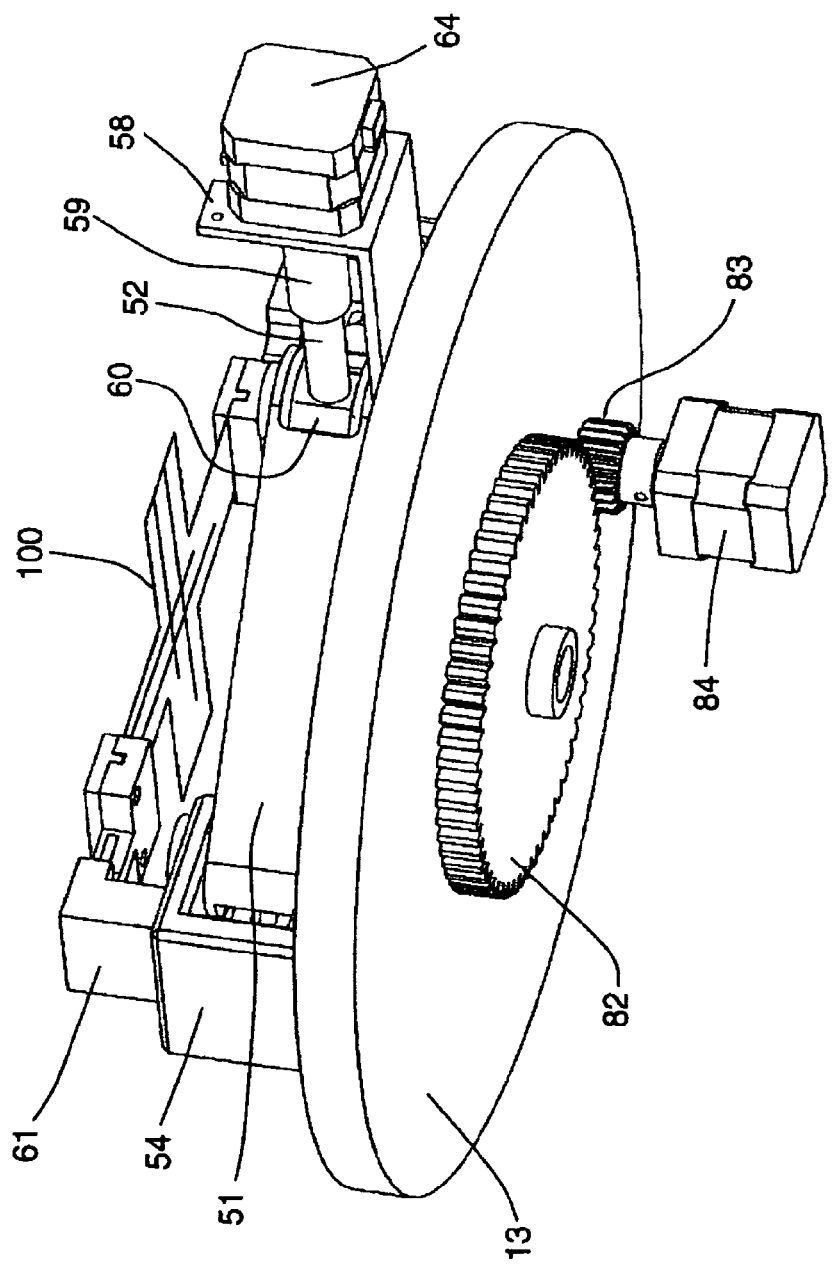
FIG. 7 depicts a perspective view of the lower scissor jack assembly, the test specimen and loading plates on the turntable with the gear system of the testing apparatus of FIG. 1.

Referring to FIGS. 5, 6 and 7, the linkages 51 of the lower scissor jack assembly 12 are hinged at screw-gear hinges 53 and 67 and two pairs of loading hinges 68. The lower scissor jack assembly 12 also includes a power screw-gear 52 and the second stepper motor 64. The loading hinges 68 are connected to two loading supports 54 on either side of the loading hinges. The axis of the screw-gear 52 is generally perpendicular and on a parallel plane to the axis of the screw-gear 22 of the upper scissor jack assembly 11. That is, in operation, the lower scissor jack assembly 12 is rotated ninety degrees with respect to the upper scissor jack assembly 11.

The screw-gear hinge 53 of the lower scissor jack assembly 12 has a nut 60 that is engaged with the screw-gear 52 and a displacement pin (not shown) that slides linearly in a slot 55 which is located on the horizontal plane of the turntable 13. The screw-gear hinge 67 has a nut 60 that is engaged with the screw-gear 52. The slots 55, on either sides of the screw-gear 52, both restrain the displacement of the screw-gear hinges 53 and 67 to a co-linear motion that is perpendicular to a reference line indicating the position of the loading hinges 68.

The loading hinges 68 have displacement pins at their inferior surface (not shown) that slide linearly in a slot (not shown) that is located on the horizontal plane of the turntable 13. The slots restrain the displacement of the loading hinges 68 to a co-linear motion that is perpendicular to a reference line indicating the position of the screw-gear hinges 53 and 67. The lower scissor jack assembly 12 is supported by the turntable 13 through the pin and slot configuration.

The lower scissor jack assembly 12 has two loading plates 61 that are rigidly attached to the loading supports 54. The loading plates 61 extend above the plane of the lower scissor jack assembly 12 such that when two ends of the test specimen 100 are clamped to the distal ends of the loading plates; the specimen does not contact the screw-gear 52. The height of the distal ends of the loading plates 61 of the lower scissor jack assembly 12 is at the same level of the height of the distal ends of the loading plate assemblies 32 of the upper scissor jack assembly 11 such that the plane of the test specimen 100 is horizontal when four sides of the specimen are clamped to the four loading plates.

The second stepper motor 64 is rigidly connected to a bracket 58 and to the turntable 13 (See FIG. 6). The shaft of the second stepper motor 64 is axially and operationally connected to the screw-gear 52 through a coupling shaft 59. The coupling shaft 59 has a pin 85 and a slot 86 (See FIG. 11) that transfers the torque of the shaft to the power screw-gear 52 while allowing limited axial displacement between the shaft and the screw-gear. There is a limiting switch 63 on the distal end of the slot 55, proximate to the screw-gear hinge 53. This limiting switch 63 is used to stop the stepper motor 64 when the hinge 53 reaches the proximal end of the slot; thereby, preventing the lower scissor jack assembly 12 from overextending.

Referring to FIG. 7, the turntable 13 comprises a planar circular disc, a gear 82, a pinion gear 83 and the third stepper motor 84. The gear 82 is coaxial to the turntable 13 and is engaged with the pinion gear 83. The third stepper motor 84 is rigidly connected to the supporting base 14 and electrically connected to the electronic driver 96 (shown in FIG. 1).

Upon energizing the third stepper motor 84, the turntable 13 can rotate clockwise or counter-clockwise, thereby rotating the lower scissor jack assembly 12 with respect to the upper scissor jack assembly 11. To restrict the angle of rotation, two contact limiting switches 30 (shown in FIG. 1 and FIG. 4) are attached to the sides of the support brackets 28. The distance between the sides and the contact limiting switches 30 of the support brackets 28 confines the maximum relative rotation of the lower scissor jack assembly 12 with respect to the upper scissor jack assembly 11. That is, the maximum shear angle of the test specimen 100 is defined by the distance between the support brackets 28 because the contact limiting switches 30 electrically stop the rotation of the turntable 13 when contacted and therefore stops shearing of the specimen.

Figure 8:
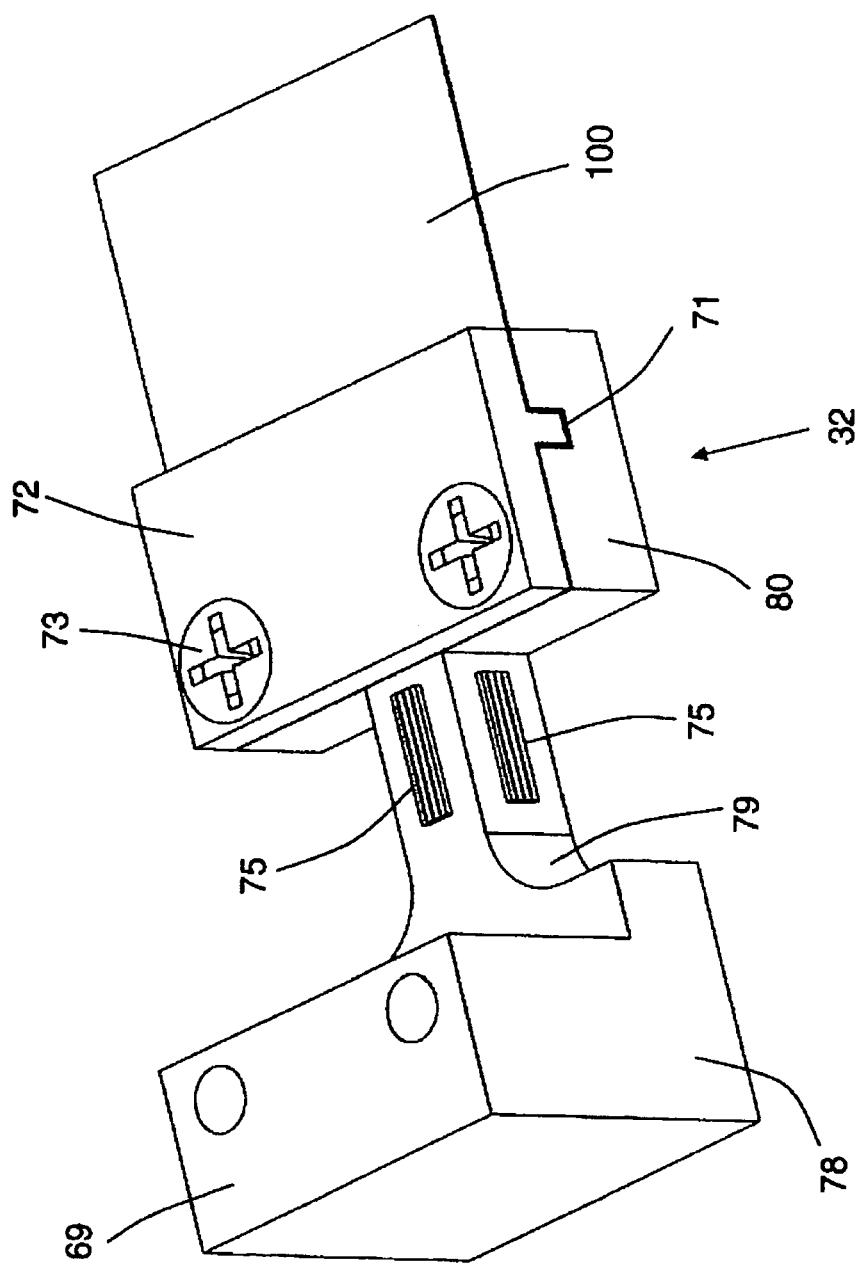
FIG. 8 depicts a perspective, view of the loading plate and the strain gauges of the testing apparatus of FIG. 1.

Referring to FIG. 8, the loading plate assembly 32 comprises an L-shape bracket 78 having an extension 79, a distal end 80 and a locking plate 72. The extension 79 has two strain gauges 75 attached to adjacent surfaces. In one embodiment, the distal end 80 has a slot 71, the locking plate 72 and a plurality of screws 73. The fabric test specimen 100 is clamped between the locking plate 72 and the slot 71 (in a tongue and groove manner) by tightening the screws 73.

Figure 9:
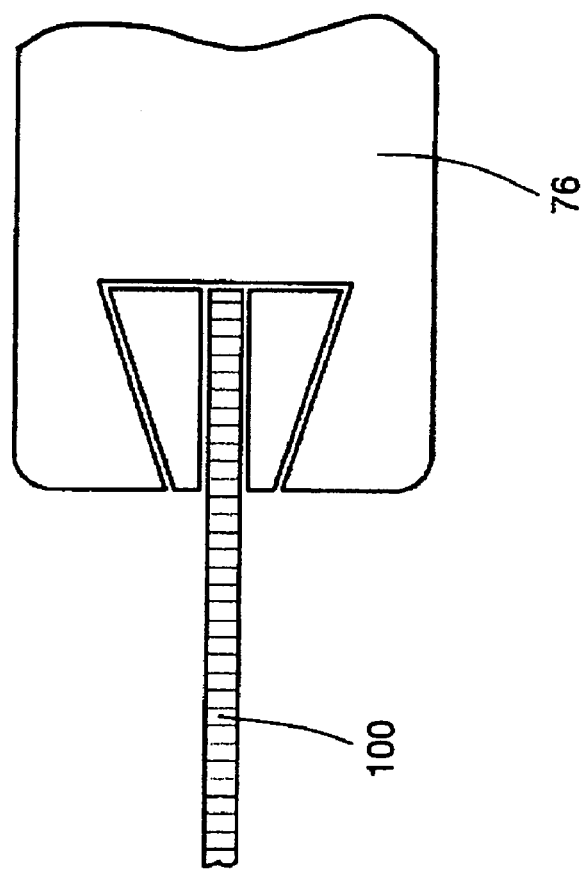
FIG. 9 depicts a first variant of the tension grip assembly of the testing apparatus of FIG. 1.
Figure 10:
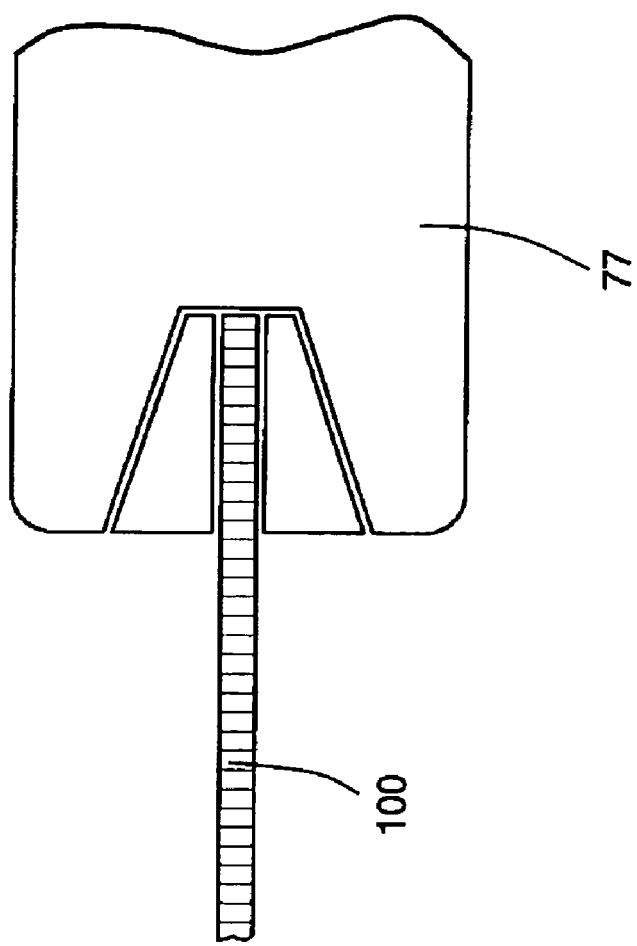
FIG. 10 depicts a first variant of the compression grip assembly of the testing apparatus of FIG. 1.

When the test specimen 100 is not a fabric, but instead is a solid object, and is to be subjected to a tension, another embodiment, may be used. The embodiment includes a standard tension grip 76 (shown in FIG. 9) will replace the distal end of the loading plate assembly 32. Likewise, when the test specimen 100 is not a fabric, but rather is a solid object, and is to be subjected to a compression, another embodiment, may be used. The embodiment which includes a compression grip 77 (shown in FIG. 10) will replace the distal end of the loading plate assembly 32. The strain gauges 75 are electrically connected to the strain gauge indicator 90 where the strain (and the stress) of the test specimen 100 in is measured.

An upper surface 69 of the bracket 78 is rigidly connected to the corresponding loading support of the upper and lower scissor jack assemblies. Specifically, the upper surface 69 of one loading plate assembly 32 is rigidly connected to the lower surface of the loading support 24. Likewise another loading plate is rigidly connected to the lower surface of the loading support 39 (See FIG. 4). Also, the upper surface 69 of the loading plate assembly 32 is rigidly connected to the upper surface of the loading support 54, on the side of lower scissor jack assembly 12, likewise an other loading plate is rigidly connected to the upper surface of the loading support 54, on the another side of the lower jack assembly 12. (See FIG. 5).

Operation of the testing assembly 10 involves clamping sides of the test specimen 100 to the distal clamping ends of the four loading plates assemblies (Note that two of the loading plate assemblies 32 are rigidly connected to the loading supports of the upper scissor jack assembly 11 and the other two of the loading plate assemblies 61 are rigidly connected to the loading supports of lower scissor jack assembly 12).

For tensile loading of planar solids, a tension grip 76 is used (See FIG. 9) and for compressive loading, a compression grip 77 is used (See FIG. 10), and for fabric, the tongue and groove clamping is used (See FIG. 8). Second, through a laptop or desktop computer and by using standard testing software or standard C++ programming; the digital computer commands are transferred to the stepper motor drivers through the data acquisition (DAQ) device. That is, through a computer command each of the stepper motors are energized and the test specimen 100 will be subjected to a combination of biaxial tension, compression or in-plane shear. The strains of the test specimen 100 will be measured by the strain gauge indicator and fed back through the DAQ device to the computer. The rotation of the turntable 13, or the angle of in-plane shear, is measured and controlled through the corresponding electronic driver.

Upon energizing the stepper motor 38 and rotating a output shaft of the stepper motor in a clockwise or counter-clockwise direction; the screw-gear hinges 33 and 65 move toward or away from each other, while the loading hinges 31 move conversely away or toward each other. Note that the movements of the hinges are restrained by the slots (29, 35) and the sliding shafts (25, 26). Therefore, by activating the gear of the motor 38 in a clockwise and a counter-clockwise rotation, the test specimen 100 will be subjected to a tension or a compression load through the direct connection of the specimen with the loading plate assemblies 32 connected to the loading supports 24 and 39.

The limiting switch 62 limits the maximum expansion of the upper scissor jack assembly 11. Likewise, upon energizing the stepper motor 64 and rotating an output shaft of the motor in a clockwise or counter-clockwise direction, the screw-gear hinges 53 and 67 move toward or away from each other, while the loading hinges 68 move conversely away or toward each other (See FIG. 5 and FIG. 6). Note that the movements of the hinges are restrained by the four slots 55 on the turntable 13. Therefore, by rotating the gear shaft of the stepper motor 64 in the clockwise or counter-clockwise direction, the test specimen 100 will be subjected to a tension or a compression load through the direct connection of the specimen with the two loading plates 61. The limiting switch 63 limits the expansion of the lower scissor jack assembly 12.

Finally, upon energizing the third stepper motor 84 in a clockwise or counter-clockwise direction; the turntable 13 including the lower scissor jack assembly 12 will turn in either the clockwise or counter-clockwise direction. Therefore, both loading plates 61 rotate in a clockwise or counter-clockwise direction and apply the in-plane shear in a clockwise or counter-clockwise to the test specimen 100.

In addition to the usage of the previously mentioned strain gauges, conventional measurement equipment systems such as force transducers can be utilized to measure forces/loads applied to the test specimen. Also, a conventional displacement wire transducer, or a conventional Linear Variable Displacement Transducer (LVDT) can be placed on the loading plates to measure the total biaxial displacements, rotation and strains of the test specimen 100.

It is important to note that the testing apparatus 10 can apply a non-equi biaxial loading ratio in that the tension/compression and the displacements in each direction can be different and independent.

A first variant of operation is to use the testing apparatus 10 for a non-orthogonal (oblique) biaxial loading of the test specimen 100. This use is particularly important for testing of braided fabrics and non-orthogonal composite materials. To accomplish this task the stepper motor 84 of the turntable 13 is energized and the angle between the two axes of the applied load, i.e., the angle between the upper and the lower jack, can be adjusted to a desired oblique test specimen.

A second variant of operation is to use the testing apparatus 10 for the alternative modes of loading the test specimen 100: uniaxial tension, uniaxial compression, biaxial tension, biaxial compression, uniaxial tension with in-plane shear, uniaxial compression with in-plane shear, biaxial tension with in-plane shear, biaxial compression with in-plane shear, unequal biaxial tension with in-plane shear and unequal biaxial compression with in-plane shear.

Figure 12:
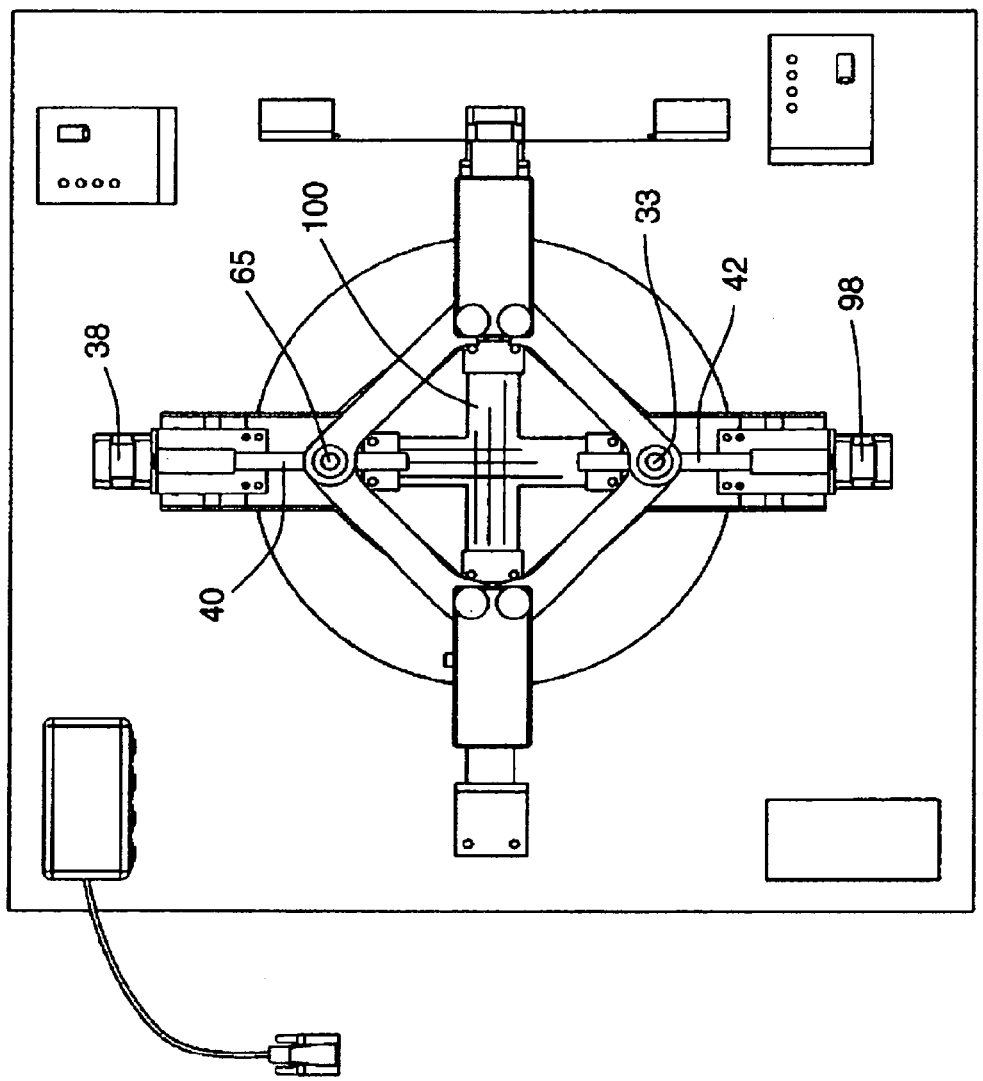
FIG. 12 depicts a variant of the power screw-gear arrangement.

An alternative power screw-gear arrangement is shown in FIG. 12 that enables visual access for viewing and video recording of the specimen 100 during testing. This alternative, which also makes installation of the test specimen 100 simpler, replaces the power screw-gear 22 with two truncated power screw-gears 40, 42 aligned along the upper axis. The truncated power screw-gears 40, 42 are operated in a synchronized manner using one stepper motor 38, 98 for each power screw-gear. The limiting switch 62 can be used to inactivate the stepper motor for each screw-gear.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. An apparatus for testing material properties of a specimen, said apparatus comprising:
    a base;
    a turntable with a first face of said turntable rotatably connected to said base about a longitudinal axis of said apparatus;
    a lower assembly supported by and parallel to said turntable on a first plane, said lower assembly having a linkage of at least four bars encompassing the longitudinal axis with each of said bars pivotable to an adjacent bar at a hinge such that there are at least two loading hinges and two screw-hinges, with said lower assembly having at least two loading plates with each loading plate capable of securing the test specimen at a second plane and with each of said loading plates affixed to at least one of two loading supports at the first plane with each of said loading supports having a clamp portion mechanically supporting said loading hinge and said linkage;
    an upper assembly on a third plane parallel to said lower assembly along the longitudinal axis, said upper assembly including a linkage of at least four bars with each of said linkage bars pivotable at a hinge to an adjacent bar such that there are at least two loading hinges and two screw-hinges with said upper assembly having at least two loading plates and each loading plate of said upper assembly affixed to a loading support and each of said loading plates having a first end on the second plane capable of securing the test specimen and with a second end of each of said loading hinges affixed to said loading support at the third plane with a first of said loading supports slidably engaging a first sliding shaft secured as part of a first upper assembly support bracket and a second of said loading supports slidably engaging a second sliding shaft secured as part of a second upper assembly support bracket with both of said support brackets affixed to said base at an opposite end from said sliding shafts;
    wherein movement of said screw-hinges of said upper assembly allows said screw-hinges to move toward each other thereby causing said loading hinges of said upper assembly to move away from each other on said loading supports along said slidable shafts of said upper assembly such that said linkage resembles a scissor-like motion for applying a tension loading to the specimen by said loading plates of said upper assembly;
    wherein movement of said screw-hinges of said upper assembly allows said screw-hinges to move away from each other thereby causing said loading hinges of said upper assembly to move toward each other on said loading supports along said slidable shafts of said upper assembly such said linkage resembles a scissor-like motion for applying a compression loading to the specimen by said loading plates of said upper assembly;
    wherein movement of said screw-hinges of said lower assembly allows said screw-hinges to move toward each other such that said linkage of said lower assembly resembles a scissor-like motion for applying a compression loading to the specimen;
    wherein movement of said screw-hinges of said lower assembly allows said screw-hinges to move away from each other such that said linkage of said lower assembly resembles a scissor-like motion for applying a tension loading to the specimen; and
    wherein rotation of said turntable about the longitudinal axis causes said loading plates of said lower assembly to rotate thereby applying torsional loading to the specimen.

2. The test apparatus in accordance with claim 1, said apparatus further comprising a first screw-gear mechanically connected to and co-planer with said linkage of said upper assembly and in alignment with said screw hinges of said upper assembly wherein rotation of said first screw-gear engages said screw hinges of said upper assembly to allow the movement of said screw-hinges to and away from each other.

3. The test apparatus in accordance with claim 2, said apparatus further comprising a first motor affixed to said base and operationally connected to said first screw-gear wherein said first motor is capable of mechanically rotating said first screw-gear.

4. The test apparatus in accordance with claim 3, said apparatus further comprising a second screw-gear mechanically connected to and co-planer with said linkage of said lower assembly and in alignment with said screw-hinges of said lower assembly wherein rotation of said second screw-gear engages said screw-hinges of said lower assembly to allow the movement of said screw-hinges to and away from each other.

5. The test apparatus in accordance with claim 4, said apparatus further comprising a second motor affixed to said turntable and operationally connected to said second screw-gear wherein said second motor is capable of mechanically rotating said second screw-gear.

6. The test apparatus in accordance with claim 5, said apparatus further comprising a third motor operationally connected to said turntable wherein said third motor is capable of rotating said turntable.

7. The test apparatus in accordance with claim 6, said upper assembly further comprising:
 a third upper assembly support bracket affixed to said base at a first face of said third upper assembly support bracket;
 a motor support bracket affixed to said third upper assembly support bracket at a second face of said third upper assembly support bracket with said motor support bracket capable of mounting said first stepper motor in operational alignment with a first of said screw hinges of said upper assembly.

8. The test apparatus in accordance with claim 7, said apparatus further comprising:
 a fourth upper assembly support bracket affixed to said base at a first face of said fourth upper assembly support bracket;
 at least one indent within a second face of said fourth upper assembly support bracket;
 wherein said at least one indent of said fourth upper assembly support bracket is capable of restraining at least one displacement pin of a second of said screw-hinges of said upper assembly such that said screw-hinges of said upper assembly remain perpendicular in movement to said loading hinges of said upper assembly.

9. The test apparatus in accordance with claim 8, said apparatus further comprising at least one limit switch proximate to said at least one indent of said fourth upper assembly support bracket wherein said at least one limit switch is capable of stopping operation of said first motor upon contact of at least one of said screw-hinges of said upper assembly.

10. The test apparatus in accordance with claim 9, said turntable of said apparatus further comprising:
 a first indent within a second face of said turntable wherein said first indent of said turntable is capable of restraining at least one displacement pin of at least one of said screw-hinges of said lower assembly such that said screw-hinges of said lower assembly remain perpendicular in movement to said loading hinges of said lower assembly; and
 a second indent within the second face of said turntable wherein said second indent is spaced apart from said first indent of said turntable and wherein said second indent is capable of restraining at least two displacement pins of said loading hinges of said lower assembly such that said loading hinges remain perpendicular in movement to said screw hinges of said lower assembly.

11. The test apparatus in accordance with claim 10, wherein said second upper support bracket comprises two spaced-apart angle brackets with a first face of each of said angle brackets affixed to said base and a connector connecting a second face of each of said angle brackets to each other;
 wherein said second sliding shaft of said upper assembly is secured at said connecting plate; and
 wherein each of said spaced-apart angle brackets has a contact limit switch on a side of each angle bracket that faces another said angle bracket such that contact on either of said contact limit switches electrically stops the rotation of said turntable.

12. The test apparatus in accordance with claim 11, said apparatus further comprising at least one strain gauge operationally connected to said lower assembly.

13. The test apparatus in accordance with claim 12, said apparatus further comprising a control system for said first stepper motor, said second stepper motor and said third stepper motor.

14. The test apparatus in accordance with claim 1, wherein said apparatus further comprises:
 a first screw-gear mechanically connected to and co-planer with said linkage of said upper assembly with said first screw-gear in alignment with a first of said screw-hinges of said upper assembly wherein rotation of said first screw-gear engages said first screw-hinges to allow the movement of said first screw-hinge; and
 a second screw mechanically connected to and co-planer with said linkage of said upper assembly with said second-screw gear in alignment with a second of said screw-hinges of said upper assembly wherein rotation of said second screw-gear engages said second screw-hinges to allow the movement of said second screw-hinge.

15. The test apparatus in accordance with claim 14, said apparatus further comprising:
 a first motor affixed to said base and operationally connected to said first screw-gear wherein said first motor is capable of mechanically rotating said first screw-gear; and
 a second motor affixed to said base and operationally connected to said second screw-gear wherein said second motor is capable of mechanically rotating said second screw-gear.

16. The test apparatus in accordance with claim 15, said apparatus further comprising a third screw-gear mechanically connected to and co-planer with said linkage of said lower assembly and in alignment with said screw-hinges of said lower assembly wherein rotation of said third screw-gear engages said screw-hinges of said lower assembly to allow the movement of said screw-hinges to and away from each other.

17. The test apparatus in accordance with claim 16, said apparatus further comprising a third motor affixed to said turntable and operationally connected to said third screw-gear wherein said third motor is capable of mechanically rotating said third screw-gear.

18. The test apparatus in accordance with claim 17, said apparatus further comprising a fourth motor operationally connected to said turntable wherein said fourth motor is capable of rotating said turntable.

19. The test apparatus in accordance with claim 18, said upper assembly further comprising:
 a third upper assembly support bracket affixed to said base at a first face of said third upper assembly support bracket; and a first motor support bracket affixed to said third upper assembly support bracket at a second face of said third upper assembly support bracket with said first motor support bracket capable of mounting said first stepper motor in operational alignment with said first screw hinge of said upper assembly.

20. The test apparatus in accordance with claim 19, said upper assembly further comprising:
a fourth upper assembly support bracket affixed to said base at a first face of said fourth upper assembly support bracket; and
a second motor support bracket affixed to said fourth upper assembly support bracket at a second face of said fourth upper assembly support bracket with said second motor support bracket capable of mounting said second stepper motor in operational alignment with said second screw hinge of said upper assembly.

21. The test apparatus in accordance with claim 20, said apparatus further comprising at least one limit switch proximate to said at least one indent of said fourth upper assembly support bracket wherein said at least one limit switch is capable of stopping operation of said first motor and second motor upon contact of said second screw-hinge of said upper assembly.

22. The test apparatus in accordance with claim 21, said turntable of said apparatus further comprising:
a first indent within a second face of said turntable wherein said first indent of said turntable is capable of restraining at least one displacement pin of at least one of said screw-hinges of said lower assembly such that said screw-hinges of said lower assembly remain perpendicular in movement to said loading hinges of said lower assembly; and
a second indent within the second face of said turntable wherein said second indent is spaced apart from said first indent of said turntable and wherein said second indent is capable of restraining at least two displacement pins of said loading hinges of said lower assembly such that said loading hinges remain perpendicular in movement to said screw hinges of said lower assembly.

* * * * *